United States Patent [19]

Donald

[11] 4,186,742
[45] Feb. 5, 1980

[54] CONTRACEPTIVE-ANTIVENEREAL DISEASE TAMPON

[75] Inventor: Jack W. Donald, El Paso, Tex.

[73] Assignee: Donald Enterprises, Inc., El Paso, Tex.

[21] Appl. No.: 888,578

[22] Filed: Jun. 9, 1978

[51] Int. Cl.² ............................................. A61F 13/20
[52] U.S. Cl. .................................................... 128/270
[58] Field of Search ............................... 128/127–131, 128/260, 263, 270, 285

[56] References Cited

U.S. PATENT DOCUMENTS

| | | | |
|---|---|---|---|
| 467,599 | 1/1892 | Abundi et al. | 128/271 |
| 639,864 | 12/1899 | Von Raitz | 128/270 |
| 969,640 | 9/1910 | Langstaff | 128/270 |
| 2,687,729 | 8/1954 | Slavin | 128/270 |
| 3,067,745 | 12/1962 | Burgeni et al. | 128/285 |
| 3,128,762 | 4/1964 | Young | 128/127 |
| 3,594,468 | 7/1971 | Saurino et al. | 128/270 |
| 3,639,561 | 2/1972 | Gordon et al. | 128/270 |
| 3,639,562 | 2/1972 | Gordon et al. | 128/270 |
| 3,691,271 | 9/1972 | Charle et al. | 128/285 |
| 3,794,029 | 2/1974 | Dulle | 128/270 |
| 3,814,809 | 6/1974 | Gordon | 128/270 |
| 3,918,452 | 11/1975 | Cornfeld | 128/270 |
| 3,995,633 | 12/1976 | Gougeon | 128/127 |
| 4,066,075 | 1/1978 | Hughes | 128/127 |
| 4,108,180 | 8/1978 | Moehrle | 128/285 |

OTHER PUBLICATIONS

The Merck Index, 9th ed., 1976, pp. 866, 984–985.

Primary Examiner—Robert W. Michell
Assistant Examiner—C. F. Rosenbaum
Attorney, Agent, or Firm—Bacon & Thomas

[57] ABSTRACT

A new concept of pregnancy and disease prevention is provided by a medicated tampon in the form of a soft, porous foam ball, which is easily insertable into the vagina to cover the cervical area and which is impregnated with a safe spectrum of antibiotics for control of venereal disease and with a contraceptive for control of pregnancy. The tampon may be inserted before intercourse to remain in place during intercourse.

14 Claims, 2 Drawing Figures

CONTRACEPTIVE-ANTIVENEREAL DISEASE TAMPON

DESCRIPTION OF THE PRIOR ART

U.S. Pat. No. 3,594,468 shows a germicidal composition.

U.S. Pat. No. 3,639,562 shows a vaginal suppository plus the use of impregnated tampon.

U.S. Pat. No. 3,691,271 shows a sanitary napkin with microcapsules filled with a bactericidal and fungicidal deodorant.

U.S. Pat. No. 3,814,809 shows the combination of a suppository and tampon with a contraceptive drug for use after exposure.

U.S. Pat. No. 3,918,452 shows to be a impregnate tampon or vaginal sponge which is treated with a contraceptive drug that is microencapsulated so that there is a sustained release of contraceptive composition before during and/or after coitus to be used with an inserter.

DETAILED DESCRIPTION OF PRESENT INVENTION

This new invention is intended to eliminate the difficulties and objections to prior art contraceptives, The over population and pandemic venereal disease necessitates a more effective and generally acceptable means of control. This invention is to provide a vaginal tampon which is impregnated with a known safe contraceptive and antibiotics, that will provide a means of the prevention of pregnancy and venereal disease. All ingredients are commercially available, and known to the art as over the counter products.

This tampon shall be a 1⅜" in diameter, spherical ball of a smooth and very fine porosity, soft light weight material such as Polyurathane-Polyether or Polyester, made by a molding process with the end of a 3" string embedded into the ball during the molding process for easy removal, of the type used in the commonly marketed tampons. These are inert materials and are non-reactive to the human body. This is to be sterilized, and dipped into a solution of Glycerin and water that contains per ounce, the following antibiotics, Zinc Bacitracin 12,000 units and Neomycin Sulphate 85 mgm. and Polymyxin B sulphate 250,000 units, together with the spermicide Nonoxynol 10%, buffered to PH 4.5.

The invention will be further understood by reference to the drawings in which.

Figures 1, 2:
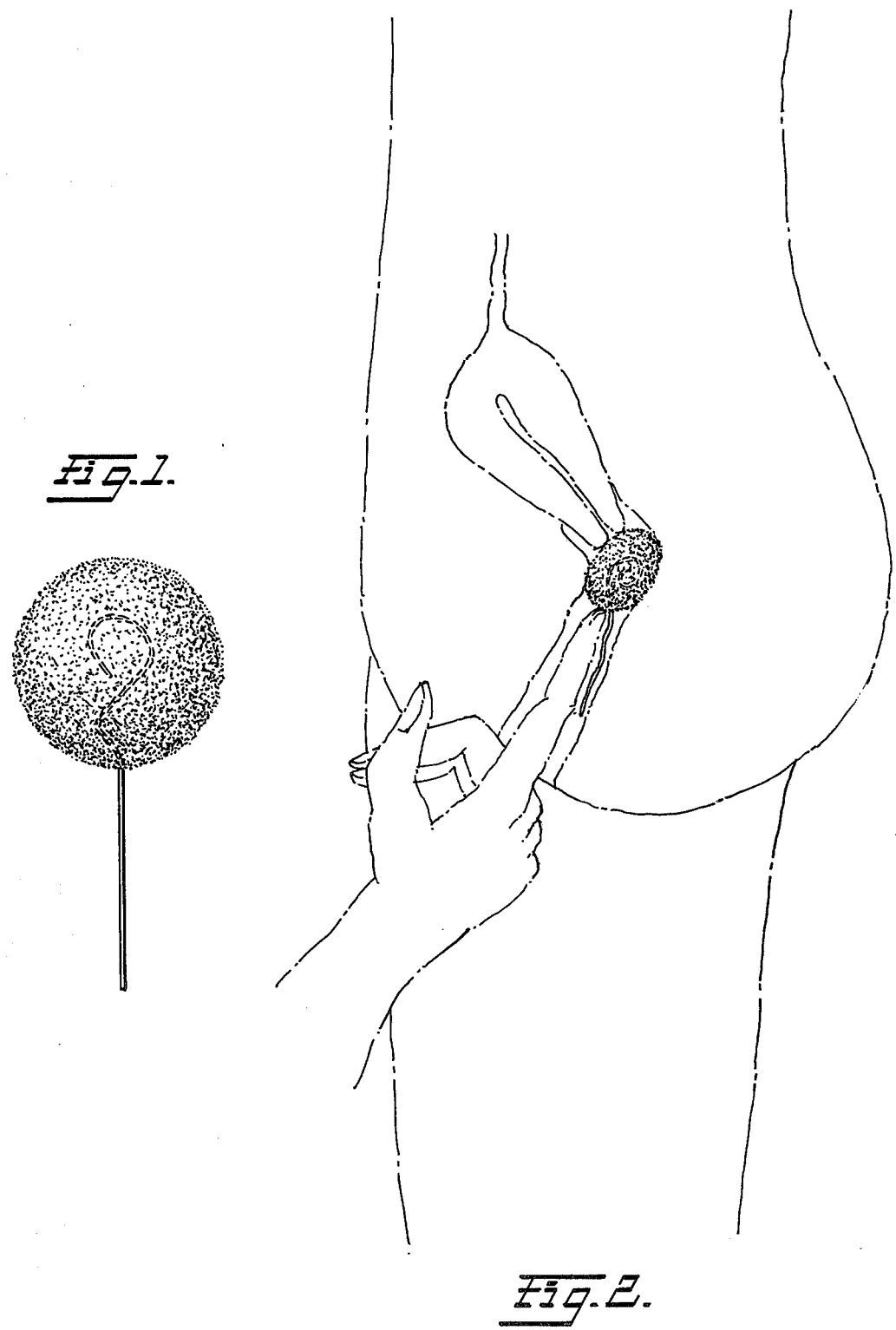
FIG. 1 is a view of the soft foam tampon of the invention in its uncompressed form prior to insertion in the vagina.
FIG. 2 is a diagrammatic illustration showing the placement of the tampon in the vagina to cover the cervical area.

The ball is to be inserted with the forefinger, high in the vagina before sexual intercourse and left at least 2 hours after intercourse. No insertion device is necessary. The foam ball should be packaged individually in a moisture proof package such as cellophane, foil or similar packaging.

Since the device is spherical in configuration it is not necessary that it be oriented prior to or after insertion. As seen in FIG. 2, it will inherently assume the configuration of the vaginal area during use.

I claim:

1. A moist medicated vaginal tampon for contraceptive and venereal disease control comprising a soft, porous foam ball of substantially spherical configuration in the uncompressed state and of a size and compressibility to fit snugly within the vagina of a human female to cover the cervix area while permitting intercourse to take place, said spherical configuration permitting easy insertion without the necessity of orientation, said porous foam ball being impregnated with a solution containing an amount of an antibiotic selected from the group consisting of salts of bacitracin, neomycin, polymyxin B and mixtures thereof effective to control venereal disease and a contraceptively effective amount of nonoxynol.

2. The vaginal tampon as defined in claim 1, wherein the shape is a foam ball of a soft, foamed material selected from the group consisting of polyurethanes, polyesters, polyethers and mixtures thereof.

3. The vaginal tampon as defined in claim 1, wherein the antibiotic agent comprises zinc bacitracin, neomycin sulphate and polymyxin B sulphate.

4. The vaginal tampon as defined in claim 1, wherein the impregnating solution comprises a mixture of water and glycerin containing said antibiotic and contraceptive agents.

5. The vaginal tampon as defined in claim 1, wherein the impregnating solution is buffered to a pH value of about 4.5.

6. The vaginal tampon as defined in claim 1, wherein the foam ball has a diameter of about 1⅜".

7. The vaginal tampon as defined in claim 1, wherein the solution comprises about 10% by weight of nonoxynol.

8. The vaginal tampon as defined in claim 1, which further comprises a string connected to the shape of porous material adapted for easy removal of the tampon from its site of application.

9. The vaginal tampon as defined in claim 1, which is contained singly in a moisture proof package.

10. A method for preventing pregnancy which comprises the step of applying to the vaginal cavity of a mammalian female the vaginal tampon as defined in claim 1 precoitus and retaining it in the vaginal cavity during sexual intercourse.

11. A method for contraceptive and venereal disease control which comprises the step of applying to the vaginal cavity of a human female the vaginal tampon as defined in claim 1 and retaining it in the vaginal cavity during intercourse.

12. A moist medicated vaginal tampon for contraceptive and veneral disease control comprising a porous foam ball of substantially spherical shape adapted to be inserted into the vagina prior to sexual intercourse without the necessity of an applicator and to be retained in the vagina during such intercourse, said ball being of a soft, light weight foam material having a very fine porosity and being impregnated with a solution of water and glycerin containing per ounce the following antibiotics in approximately the amounts specified, 12,000 units of zinc bacitracin, 85 mgm. of neomycin sulphate, 250,000 units of polymycin B sulphate, together with the spermicide nonoxynol in 10% concentration in the solution, and said solution being buffered to a pH of approximately 4.5.

13. A method for preventing pregnancy which comprises the step of applying to the vaginal cavity of a mammalian female the vaginal tampon as defined in claim 12 precoitus and retaining it in the vaginal cavity during sexual intercourse.

14. A moist, medicated vaginal tampon for contraceptive and venereal disease control, comprising a shape of physiologically inert, soft, porous, light weight foam material which is insertable in the vagina prior to intercourse without the necessity of an applicator, said shape being impregnated with a solution comprising per one ounce about 12,000 units of zinc bacitracin, 85 mgm. of neomycin sulphate and 250,000 units of polymyxin B sulphate for venereal disease control and with a contraceptively effective amount of a contraceptive agent.

* * * * *